United States Patent
Zolotov

(10) Patent No.: US 9,055,970 B2
(45) Date of Patent: Jun. 16, 2015

(54) SKIN GRAFT PREPARATION DEVICE

(71) Applicant: Zimmer Surgical, Inc., Dover, OH (US)

(72) Inventor: Aleksandr Zolotov, North Canton, OH (US)

(73) Assignee: Zimmer Surgical, Inc., Dover, OH (US)

(*) Notice: Subject to any disclaimer, the term of this patent is extended or adjusted under 35 U.S.C. 154(b) by 246 days.

(21) Appl. No.: 13/650,271

(22) Filed: Oct. 12, 2012

(65) Prior Publication Data

US 2014/0107668 A1    Apr. 17, 2014

(51) Int. Cl.
*A61B 17/50* (2006.01)
*A61B 17/322* (2006.01)

(52) U.S. Cl.
CPC ....... *A61B 17/322* (2013.01); *A61B 2017/3225* (2013.01)

(58) Field of Classification Search
CPC ................. A61B 17/322; A61B 2017/3225; A61B 2017/00761; A61B 2017/320004
USPC .................................... 606/131–133; 600/36
See application file for complete search history.

(56) References Cited

U.S. PATENT DOCUMENTS

| | | | |
|---|---|---|---|
| 5,004,468 A | 4/1991 | Atkinson | |
| 5,196,020 A * | 3/1993 | Atkinson et al. | 606/132 |
| 5,306,279 A | 4/1994 | Atkinson | |
| 6,063,094 A | 5/2000 | Rosenberg | |
| 7,625,384 B2 | 12/2009 | Eriksson et al. | |
| 8,187,285 B2 * | 5/2012 | Eriksson et al. | 606/132 |
| 2004/0230215 A1 | 11/2004 | Eriksson et al. | |
| 2010/0042127 A1 | 2/2010 | Eriksson et al. | |
| 2011/0077664 A1 | 3/2011 | Schulz et al. | |

FOREIGN PATENT DOCUMENTS

| WO | 9720509 A2 | 6/1997 |
|---|---|---|
| WO | 2004075764 A1 | 9/2004 |

OTHER PUBLICATIONS

Fossum, Magdelena, et al., Minced Skin for Tissue Engineering of Epitheliazed Subcutaneous Tunnels, Tissue Engineering: Part A vol. 15, No. 8 2009, pp. 2085-2092.
Xpansion Skin Graft Instrument Kit, Applied Tissue Technologies, Brochure 2011.
The Rosenberg Adjustable Skin Graft Mesher, 4Med, Ltd., Instructions, 5 pgs.

(Continued)

*Primary Examiner* — Victor Nguyen
(74) *Attorney, Agent, or Firm* — Seager, Tufte & Wickhem LLC

(57) ABSTRACT

A skin graft mesher including a cutting roller and a guide roller rotatably mounted to a fixture. A skin graft may be advanced through the mesher between the rollers to form a pattern of perforations in the skin graft. The cutting roller includes cutting rings disposed on an axle and rotatable therewith. The cutting roller further includes a tissue clearing structure positioned between adjacent cutting rings with the axle extending through the tissue clearing structure and rotatable relative to the tissue clearing structure. The tissue clearing structure may clear tissue from between adjacent cutting rings during operation of the skin graft mesher. The tissue clearing structure may be eccentrically rotated about the axle between adjacent cutting rings with the tissue clearing structure extending radially outward beyond the outer diameter of the cutting ring around less than the entire outer circumference of the cutting ring.

24 Claims, 10 Drawing Sheets

(56) References Cited

OTHER PUBLICATIONS

The Humeca skin graft mesher and V-carriers, Humeca Brochure, 2008, 8 pgs.

Brennen Skin Graft Mesher, Integra LifeSciences Corp. Brochure, 2 pgs.

Aesculap Power Systems Skin Graft Mesher, Braun Brochure 2006, 2 pgs.

* cited by examiner

SKIN GRAFT PREPARATION DEVICE

TECHNICAL FIELD

The disclosure is directed to an apparatus for preparing a skin graft. More particularly, the disclosure is directed to cutting members for a skin graft preparation device incorporating cutting blade clearing features.

BACKGROUND

Skin graft meshers may be used to prepare skin or synthetic material for a skin graft in such a way that a small area of skin or synthetic material may be expanded to be grafted over a larger area on the patient. Some such skin graft meshers, such as the skin graft preparation apparatus disclosed in U.S. Pat. No. 5,004,468, which is incorporated herein by reference, utilize cutting rollers to provide a pattern of perforations or cuts in the skin graft to permit the skin graft to be expanded. In some instances, the skin graft may stick or adhere to the cutting roller as the skin graft is passed by the cutting roller, thus making it challenging to separate the skin graft from the cutting roller, which may result in damaging the skin graft. Accordingly, there is a need to provide means for separating the skin graft from the cutting roller without damaging the skin graft.

SUMMARY

The disclosure is directed to several alternative designs, materials and methods of manufacturing skin graft preparation device components and assemblies, and uses thereof.

Accordingly, one illustrative embodiment is a skin graft preparation device. The skin graft preparation device includes a housing, and a cutting member rotatably mounted to the housing. The cutting roller includes an axle having a longitudinal axis and a plurality of cutting segments disposed on the axle and rotatable with the axle through rotation of the axle about the longitudinal axis. The cutting member further includes a tissue clearing structure positioned between adjacent cutting segments with the axle extending through the tissue clearing structure and rotatable relative to the tissue clearing structure. The tissue clearing structure is configured to clear tissue from between adjacent cutting segments during operation of the skin graft preparation device.

Another illustrative embodiment is a cutting member for a skin graft preparation device. The cutting member includes an axle having a longitudinal axis and a plurality of cutting segments disposed on the axle and rotatable with the axle through rotation of the axle. Each cutting ring has an outer circumference and an outer diameter. The cutting member further includes a tissue clearing structure positioned on and configured to rotate eccentrically about the axle between adjacent cutting segments. The tissue clearing structure is configured to extend radially outward beyond the outer diameter of the cutting segment around less than the entire outer circumference of the cutting segment.

Another illustrative embodiment is a cutting member for a skin graft preparation device including an axle having a longitudinal axis. The cutting member also includes a first cutting segment, a second cutting segment, a third cutting segment, and a fourth cutting segment, each disposed on the axle and rotatable with the axle through rotation of the axle. Each of the first, second, third and fourth cutting segments includes one or more cutting blades circumferentially arranged around an outer perimeter of the cutting segment. The cutting member further includes a first clearing structure, a second clearing structure and a third clearing structure. The first tissue clearing structure is positioned on the axle between the first and second cutting segments, wherein a first point on an outer periphery of the first tissue clearing structure extends radially outward from the longitudinal axis of the axle to or beyond the outer perimeters of the first and second cutting segments while a second point on the outer periphery of the first tissue clearing structure does not extend radially outward from the longitudinal axis of the axle to the outer perimeters of the first and second cutting segments. The second tissue clearing structure is positioned on the axle between the second and third cutting segments, wherein a first point on an outer periphery of the second tissue clearing structure extends radially outward from the longitudinal axis of the axle to or beyond the outer perimeters of the second and third cutting segments while a second point on the outer periphery of the second tissue clearing structure does not extend radially outward from the longitudinal axis of the axle to the outer perimeters of the second and third cutting segments. The third tissue clearing structure positioned is on the axle between the third and fourth cutting segments, wherein a first point on an outer periphery of the third tissue clearing structure extends radially outward from the longitudinal axis of the axle to or beyond the outer perimeters of the third and fourth cutting segments while a second point on the outer periphery of the third tissue clearing structure does not extend radially outward from the longitudinal axis of the axle to the outer perimeters of the third and fourth cutting segments.

Yet another illustrative embodiment is a method of forming cuts in a skin graft. The method includes rotating a cutting member of a skin graft preparation device about a longitudinal axis of an axle of the cutting member, whereby cutting blades of a plurality of cutting segments of the cutting member penetrate into or through the skin graft to form cuts in the skin graft such that portions of the skin graft are positioned between adjacent cutting segments. The method further includes disengaging portions of tissue of the skin graft from between adjacent cutting segments with a tissue clearing structure disposed on the axle between the adjacent cutting segments by pushing the tissue radially outward beyond an outer perimeter of the cutting segments of the cutting member.

The above summary of some example embodiments is not intended to describe each disclosed embodiment or every implementation of the aspects of the disclosure.

BRIEF DESCRIPTION OF THE DRAWINGS

The aspects of the disclosure may be more completely understood in consideration of the following detailed description of various embodiments in connection with the accompanying drawings, in which.

Figure 1:
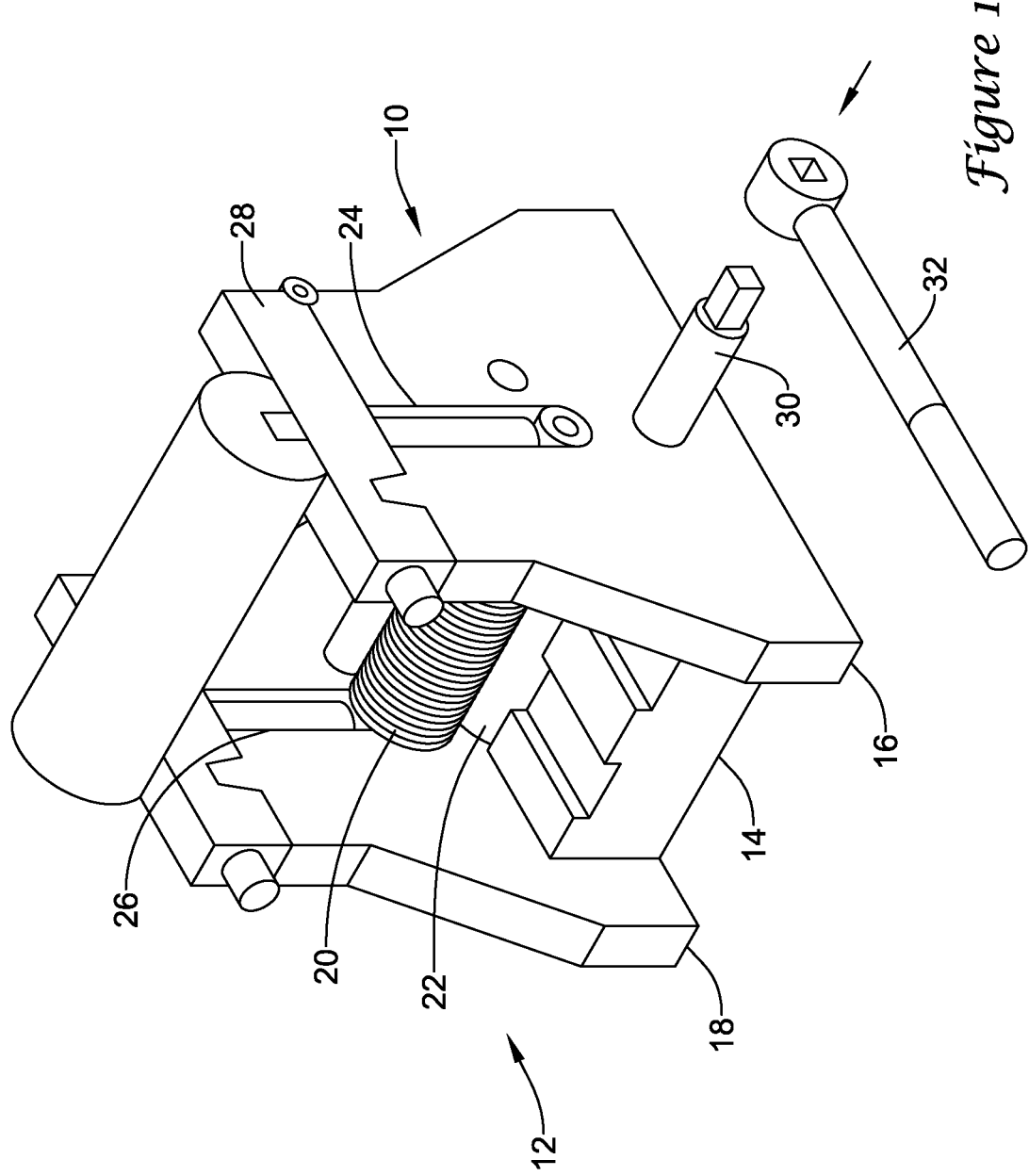
FIG. 1 is a perspective view of an exemplary embodiment of a skin graft mesher.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used herein, the term "skin graft" is intended to mean a graft formed from any and all biologically compatible materials including natural, synthetic and any combination of natural and synthetic materials that may be used for the treatment of cutaneous wounds by implanting the graft into or on a wound. Such skin grafts may be made from human skin, animal skin, synthetic or semi-synthetic materials, for example.

As used herein, the terms "skin material" and "tissue" are intended to mean any material used to form a skin graft or any material residue excised upon formation of a skin graft.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

An exemplary skin graft preparation device, illustrated as a skin graft mesher 10, is shown in FIG. 1. The skin graft mesher 10 may be configured for forming perforations or cuts (e.g., slits) in a skin graft. The skin graft mesher 10 may include a housing, such as a fixture 12 having a base 14 and a pair of opposed supports 16, 18 connected thereto and spaced apart from one another. In some embodiments, the first and second supports 16, 18 may extend generally perpendicular from the base 14 and may be generally parallel to one another.

The skin graft mesher 10 may also include a cutting member configured for forming perforations or cuts (e.g., slits) in a skin graft. In some instances, the cutting member may be a cutting roller 20. Further discussion of the cutting member of the skin graft mesher 10 will be described with respect to the illustrative cutting roller 20, however, it is noted that features of the cutting roller 20 described herein may be incorporated into a cutting member of a different construction, as desired. The skin graft mesher 10 may also include a guide roller 22 extending parallel and spaced away from the cutting roller 20. The cutting roller 20 and the guide roller 22 may each be rotatably coupled to the housing (e.g., the fixture 12), such as rotatably coupled to and extending between the first and second spaced apart supports 16, 18. For instance, a first end portion of the guide roller 22 and a first end portion of the cutting roller 20 may be rotatably coupled to the first support 16, and a second end portion of the guide roller 22 and a second end portion of the cutting roller 20 may be rotatably coupled to the second support 18.

In some embodiments, the cutting roller 20 may be removable from the fixture 12 such that the cutting roller 20 may be cleaned, sterilized, repaired, replaced, or exchanged for a different cutting roller 20, such as a cutting roller 20 having a different skin graft cutting ratio. For example, the supports 16, 18 may include a pair of aligned slots 24, 26, respectively, configured to removably receive the first and second end portions of the cutting roller 20 therein. The fixture 12 may include means for retaining the end portions of the cutting roller 20 in the slots 24, 26. For instance, the fixture 12 may include a cover 28 pivotably coupled to the supports 16, 18. The cover 28 may retain the cutting roller 20 in the slots 24, 26 when pivoted to the closed position, shown in FIG. 1. However, the cover 28 may be pivoted to an open position to permit the cutting roller 20 to be removed from the slots 24, 26. In other embodiments, the skin graft mesher 10 may include a different structure for removably or permanently mounting the cutting roller 20 to the fixture 12.

As shown in FIG. 1, the guide roller 22 may include a shaft 30 extending from the fixture 12 which may be used to rotate the guide roller 22. For example, the shaft 30, which may be an extension of the axle 39 of the guide roller 22 in some instances, may be connected to an actuation mechanism to provide rotational motion to the guide roller 22. For instance, a handle 32 may be coupled to the shaft 30 to manually rotate the guide roller 22 in the fixture 12. In other embodiments, the shaft 30 may be coupled to a motor or other actuation mechanism. For example, a motorized actuator may be coupled to the shaft 30 and may be selectively operated to generate rotational motion.

Figure 5:
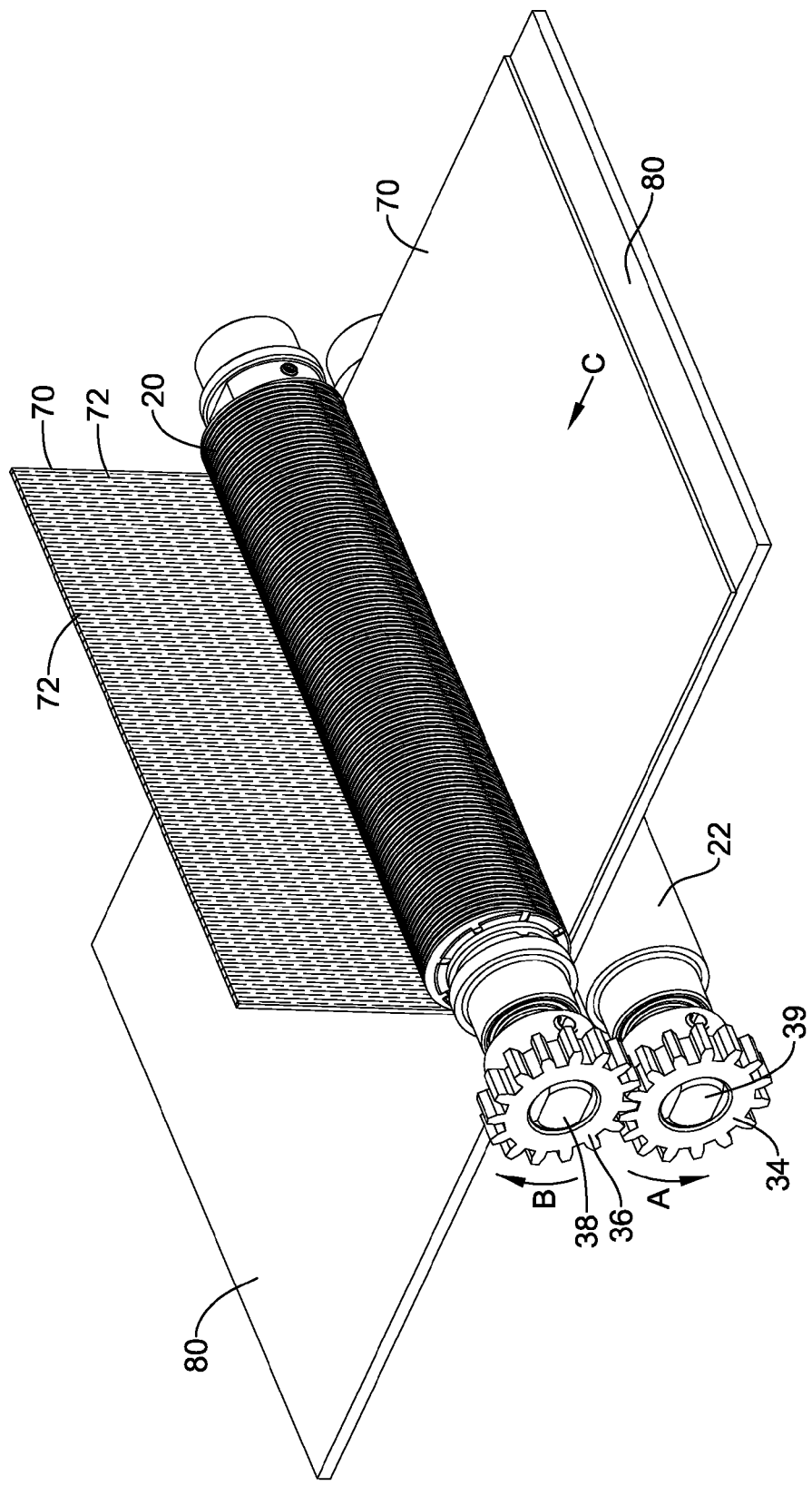
FIG. 5 is a perspective view illustrating the use of the cutting roller of FIG. 2 to form perforations or cuts in a skin graft.

Drive means may interconnect the guide roller 22 with the cutting roller 20 to transmit rotational motion between the guide roller 22 and the cutting roller 20. Accordingly, rotational movement of the guide roller 22 may be transmitted to the cutting roller 20 to effect rotational movement of the cutting roller 20. For example, as shown in FIG. 5, a gear 34 may be mounted to the axle 39 of the guide roller 22. The gear 34 may be enmeshed with a gear 36 mounted on the axle 38 of the cutting roller 20 to transfer rotational motion from the guide roller 22 to the cutting roller 20. Thus, rotation of the handle 32 may generate rotation of the guide roller 22 and opposite rotation of the cutting roller 20, via the axle 39 of the guide roller 22, the gear 34, the gear 36 and the axle 38 of the cutting roller 20. For instance, clockwise rotation of the handle 32 may result in clockwise rotation of the guide roller 22 and counter-clockwise rotation of the cutting roller 20, whereas counter-clockwise rotation of the handle 32 may result in counter-clockwise rotation of the guide roller 22 and clockwise rotation of the cutting roller 20.

Figure 2:
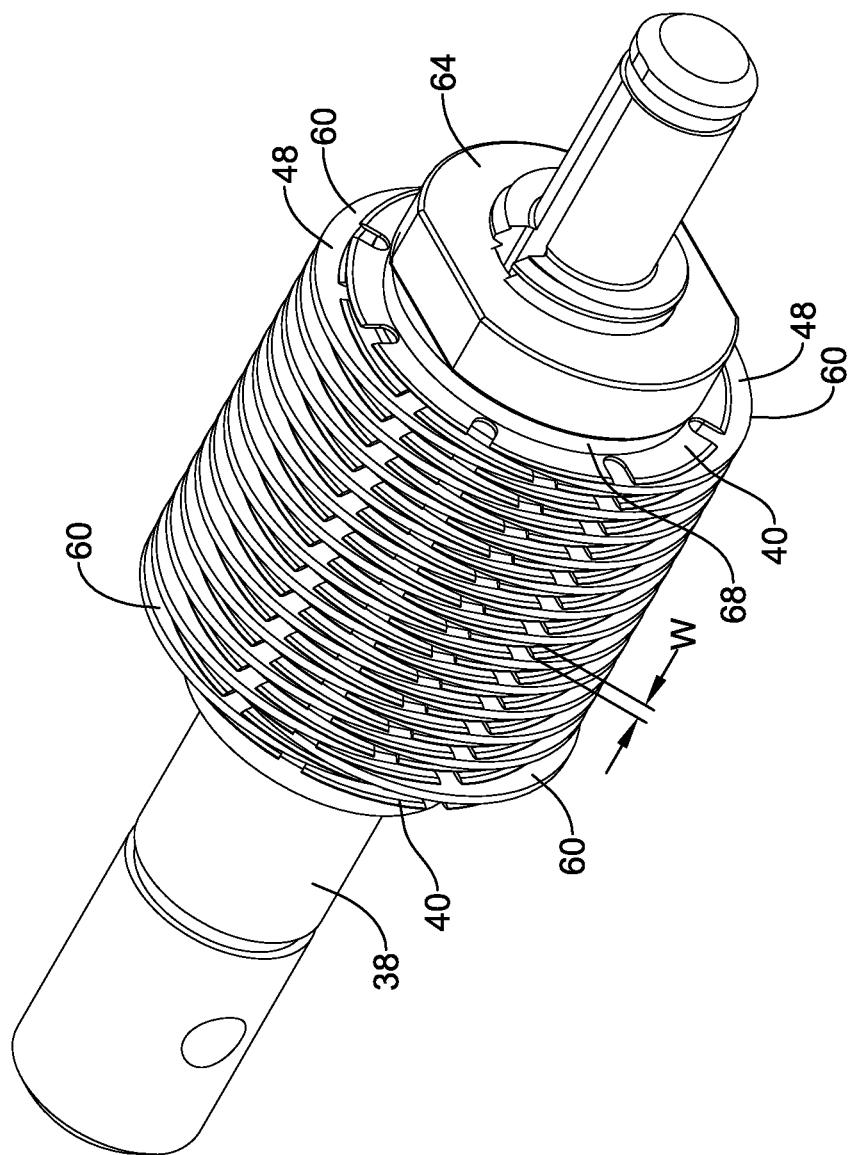
FIG. 2 is a perspective view of an exemplary cutting roller of the skin graft mesher of FIG. 1.

The cutting roller 20 may be configured to form a desired pattern of perforations or cuts (e.g., slits) in a skin graft to permit the skin graft to be stretched to a desired ratio of surface expansion, such as a 1.5:1, 3:1, 6:1, 9:1, 12:1 or 15:1 ratio of expansion. For example, as shown in FIG. 2, the cutting roller 20 may include a plurality of cutting segments, such as cutting rings 40 mounted on the axle 38 of the cutting roller 20. While in the illustrative embodiment depicts the cutting segments of the cutting roller 20 as cutting rings 40, in other embodiments, the cutting segments may have a different configuration. Further discussion of the cutting segments will be described with respect to the illustrative cutting rings 40, however, it is noted that features of the cutting rings 40 described herein may be incorporated into a cutting segment of a different construction, as desired. The configuration and arrangement of the cutting segments (e.g., cutting rings 40) may control the perforation or cut (e.g. slit) pattern imparted on the skin graft. In some instances, a set of cutting rollers 20 having different spacings of cutting rings 40 and/or different amounts of notches 52 may be provided and selected for a desired ratio of skin graft expansion.

Figure 3:
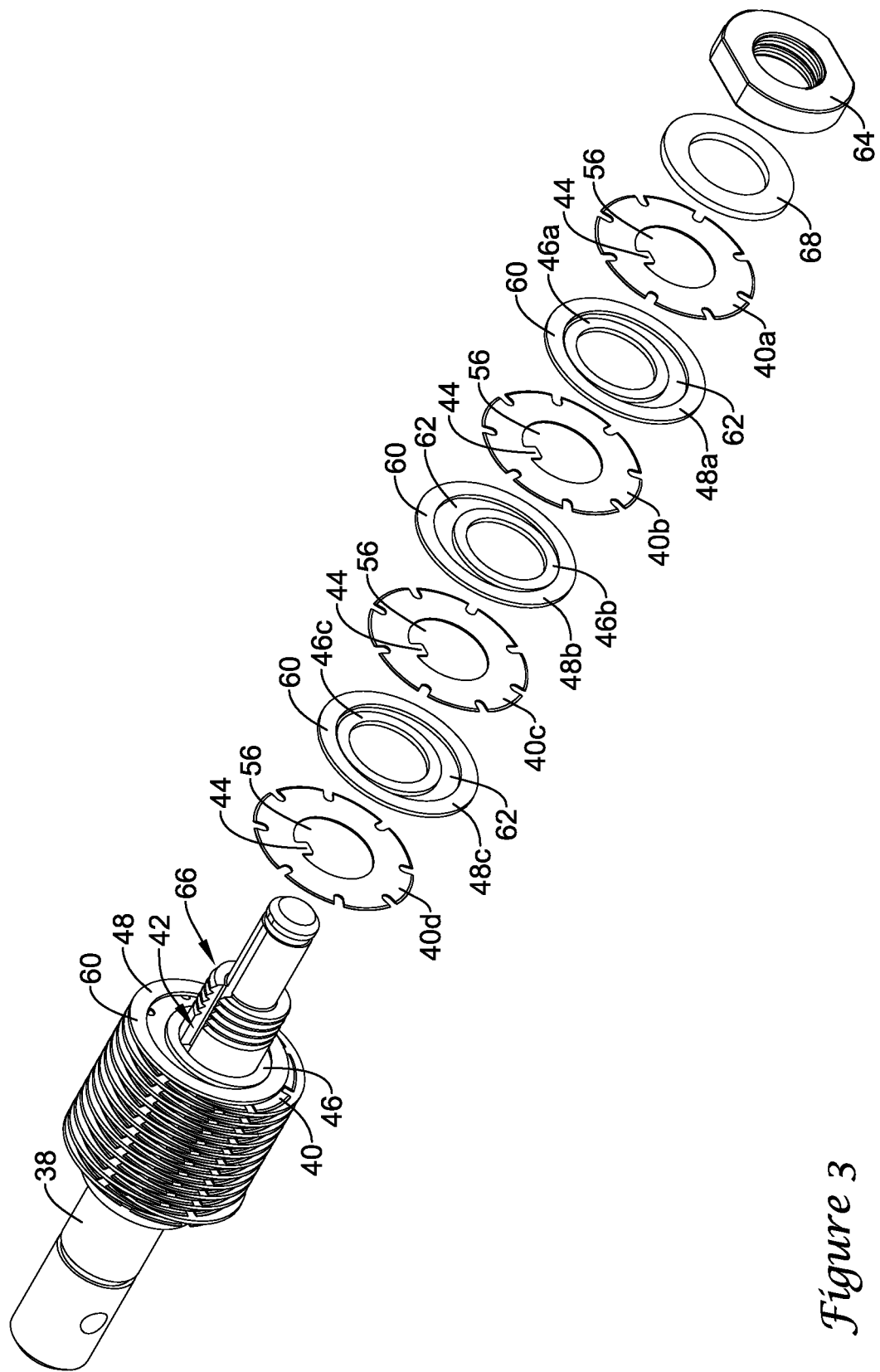
FIG. 3 is an exploded view of the cutting roller depicted in FIG. 2.

FIG. 3 is an exploded view illustrating components of an exemplary cutting roller 20, including the cutting rings 40. The cutting rings 40 may include an opening 56 for receiving the axle 38 therethrough, such that the cutting rings 40 surround the axle 38. The cutting rings 40 may be arranged on the axle 38 such that adjacent cutting rings 40 are spaced apart a predetermined distance W along the central longitudinal axis X of the axle 38 of the cutting roller 20, which controls the spacing of adjacent rows of cuts of the cut pattern imparted on the skin graft. While the exemplary cutting rings 40 are illustrated as having a circular shape, it is noted that in other embodiments the cutting rings 40 may have a different shape, if desired.

For illustrative purposes, a first cutting ring 40a, a second cutting ring 40b, a third cutting ring 40c and a fourth cutting ring 40d are shown in FIG. 3, however, the cutting roller 20 may include as many cutting rings 40 as desired to provide the desired meshing pattern on the selected width of skin graft. For example, 10 or more, 20 or more, 30 or more, 40 or more, or 50 or more cutting rings 40 may be similarly mounted on the axle 38, as desired. The plurality of cutting rings 40 (e.g., the first, second, third and fourth cutting rings 40a, 40b, 40c, 40d) may be disposed on the axle 38 and rotatable with the axle 38 through rotation of the axle 38. For example, the cutting rings 40 may include a keyed interface configured to mate with a keyed interface of the axle 38 such that rotation of the axle 38 about the central longitudinal axis X causes corresponding rotation of the cutting rings 40 about the central longitudinal axis X. For instance, as shown in FIG. 3, the axle 38 may include an elongated slot or keyway 42 extending longitudinally along the axle 38 and the cutting rings 40 may include a tab or key 44 extending into the slot or keyway 42. In other embodiments, the axle 38 may include an elongate tab extending longitudinally along the axle 38 and the cutting rings 40 may include a recess or cut-out for receiving the tab, for example. In yet other embodiments, the axle 38 may have a non-circular (e.g., polygonal) cross-section and the opening 56 of the cutting rings 40 may have a corresponding non-circular (e.g., polygonal) cross-section for receiving the axle 38 therethrough. Accordingly, the plurality of cutting rings 40 may be disposed on the axle 38 and rotatable with the axle 38 through rotation of the axle 38 about the central longitudinal axis X.

Figure 4:
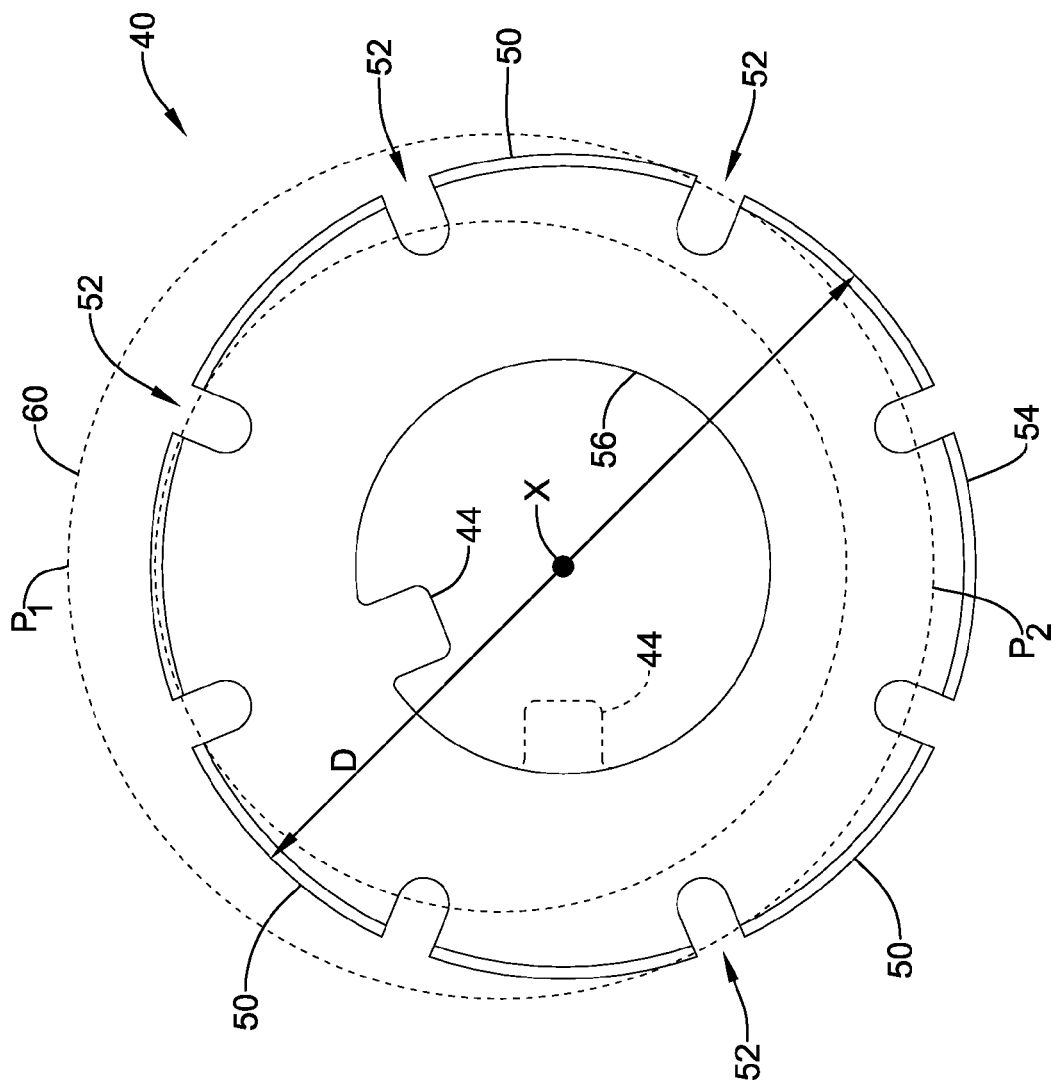
FIG. 4 is a plan view of an exemplary cutting ring of the cutting roller of FIG. 2.

FIG. 4 illustrates a cutting ring 40 including a plurality of cutting blades 50 extending circumferentially around the outer perimeter (e.g., outer circumference) 54 of the cutting ring 40. Each cutting blade 50 may be spaced from adjacent cutting blades 50 by a notch 52 in the cutting ring 40, forming a serrated or discontinuous cutting edge around the outer circumference 54 of the cutting ring 40.

The cutting rings 40 may be mounted on the axle 38 such that the cutting blades 50 of adjacent cutting rings 40 are not axially aligned with one another (i.e., the cutting blades 50 of adjacent cutting rings 40 may be staggered). For example, the second cutting ring 40b may be disposed on the axle 38 such that the cutting blades 50 of the second cutting ring 40b are not axially aligned with (i.e., staggered) the cutting blades 50 of the first cutting ring 40a. Similarly, the third cutting ring 40c may be disposed on the axle 38 such that the cutting blades 50 of the third cutting ring 40c are not axially aligned with the cutting blades 50 of the second cutting ring 40b (i.e., staggered orientation of cutting blades 50). In some instances, the cutting blades 50 of the third cutting ring 40c may be axially aligned with the cutting blades 50 of the first cutting ring 40a, or the cutting blades 50 of the third cutting ring 40c may not be axially aligned with the cutting blades 50 of the first cutting ring 40a (i.e., staggered orientation of cutting blades 50). Furthermore, in the illustrative embodiment, the fourth cutting ring 40d may be disposed on the axle 38 such that the cutting blades 50 of the fourth cutting ring 40d are not axially aligned with the cutting blades 50 of the third cutting ring 40c (i.e., staggered orientation of cutting blades 50). In some instances, the cutting blades 50 of the fourth cutting ring 40d may be axially aligned with the cutting blades 50 of the second cutting ring 40b.

For example, as shown in FIG. 4, the keying interface (e.g., the tab or key 44) of each cutting ring 40 may orient the cutting blades 50 at a desired circumferential orientation about the axle 38. For example, the keying interface (e.g., the tab or key 44) may stagger the notches 52 of adjacent cutting rings 40 to maintain cutting rings 40 in a distinct circumferential orientation different from adjacent cutting rings 40 (e.g., staggered orientation). For instance, the keying feature (e.g., the tab or key 44) of the first and third cutting rings 40a, 40c (e.g., cutting ring N, N+2, N+4, N+6, N+8, etc.) may be located radially aligned with a center point of a cutting blade 50, while the keying feature (e.g., the tab or key 44), shown in dashed lines, of the second and fourth cutting rings 40b, 40d (e.g., cutting ring N+1, N+3, N+5, N+7, N+9, etc.) may be located radially aligned with a center point of a notch 52 between adjacent cutting blades 50. Accordingly, when the cutting rings 40 are mounted on the axle 38, the position of the center of the cutting blades 50 of one cutting ring 40 may alternate with the center of the notches 52 of an adjacent cutting ring 40.

The cutting roller 20 may also include a plurality of spacers 46 positioned between adjacent cutting rings 40 configured to space the adjacent cutting rings 40 apart a desired distance. In some instances the spacers 46 may be discrete members separate from the cutting rings 40, however, in other instances, the spacers 46 may be a formed as a unitary portion of a cutting ring 40. The spacers 46 may include an opening configured to receive the axle 38 therethrough, such that the spacers 46 surround the axle 38. For illustrative purposes, a first spacer 46a positioned between and spacing apart the first and second cutting rings 40a, 40b, a second spacer 46b positioned between and spacing apart the second and third cutting rings 40b, 40c, and a third spacer 46c positioned between and spacing apart the third and fourth cutting rings 40c, 40d are shown in FIG. 3, however, the cutting roller 20 may include 10 or more, 20 or more, 30 or more, 40 or more, or 50 or more spacers 46 similarly mounted on the axle 38 between adjacent cutting rings 40, as desired. The plurality of spacers 46 (e.g., the first, second and third spacers 46a, 46b, 46c), may be configured to maintain a desired spacing between adjacent cutting rings 40 as desired. In some embodiments, the cutting rings 40 may be spaced away from adjacent cutting rings 40 by a distance of 1.2 millimeters or less, 1.0 millimeters or less, 0.8 millimeters or less, 0.6 millimeters or less, or 0.4 millimeters or less, for example.

The cutting roller 20 may also include a tissue clearing structure 48 positioned between adjacent cutting rings 40 configured to clear tissue from between adjacent cutting rings 40 during operation of the skin graft mesher 10. The axle 38 may extend through the tissue clearing structure 48 and be rotatable relative to the tissue clearing structure 48. Thus, the tissue clearing structure 48 may surround and be freely rotatable about the axle 38. In the illustrative embodiment, the tissue clearing structure 48 may surround and be freely rotatable about the spacer 46 between adjacent cutting rings 40. The thickness of the tissue clearing structure 48 (measured in an axial direction) may be smaller than the thickness of the spacer 46 (measured in an axial direction), thus permitting free rotation of the tissue clearing structure 48 around the spacer 46 and axle 38 between adjacent cutting rings 40. For illustrative purposes, a first tissue clearing structure 48a positioned between the first and second cutting rings 40a, 40b, a second tissue clearing structure 48b positioned between the second and third cutting rings 40b, 40c, and a third tissue clearing structure 48c positioned between the third and fourth cutting rings 40c, 40d are shown in FIG. 3, however, the cutting roller 20 may include 10 or more, 20 or more, 30 or more, 40 or more, or 50 or more tissue clearing structures 48 similarly mounted on the axle 38 between adjacent cutting rings 40, as desired. Each tissue clearing structure 48 may be distinct from and separated from adjacent tissue clearing structures 48 mounted on the axle 38 and be positioned between a single pair of cutting rings 40, or a tissue clearing structure 48 may include portions positioned between a plurality of pairs of cutting rings 40, if desired.

In some instances, the tissue clearing structure 48 may be a tissue clearing ring 60 disposed circumferentially around the axle 38 between adjacent cutting rings 40. For example, the tissue clearing structure 48, such as a tissue clearing ring 60, may include an opening 62 through which the axle 38 extends and may be spaced radially outward of the spacer 46 between adjacent cutting rings 40. In some instances, the diameter of the opening 62 may be greater than the outer diameter of the spacer 46 such that the tissue clearing structure 48, such as the tissue clearing ring 60, is moveable in a direction perpendicular to the central longitudinal axis X of the axle 38. Thus, the tissue clearing ring 60 may be eccentrically positioned relative to the central longitudinal axis X of the axle 38 such that the central axis of the tissue clearing ring 60 is offset away from the central longitudinal axis X of the axle 38. While the exemplary tissue clearing rings 60 are illustrated as having a circular shape, it is noted that in other embodiments the tissue cutting rings 60 may have a different shape, if desired.

As shown in FIG. 4, the tissue clearing structure 48, shown as a tissue clearing ring 60, may extend radially outward beyond the outer diameter D of the cutting ring 40 around less than the entire outer circumference 54 of the cutting ring 40, and the tissue clearing structure 48, shown as a tissue clearing ring 60, may move radially inward of the outer diameter D of the cutting ring 40 about at least a portion of the outer circumference 54 of the cutting ring 40 to permit the cutting blades 50 to contact the skin graft to form cuts or perforations (e.g., slits) in the skin graft. For example, the tissue clearing structure 48 may be eccentrically positioned relative to the central longitudinal axis X with a portion of the tissue clearing structure 48 extending outward beyond the outer diameter D of the cutting ring 40 around less than the entire outer circumference 54 of the cutting ring 40. For instance, a first point $P_1$ on an outer periphery of the tissue clearing structure 48 (e.g., the tissue clearing ring 60) may extend radially outward from the central longitudinal axis X of the axle 38 to or beyond the outer circumference 54 of the cutting ring 40 while a second point $P_2$ on the outer periphery of the tissue clearing structure 48 (e.g., the tissue clearing ring 60) does not extend radially outward from the central longitudinal axis X of the axle 38 to the outer circumference 54 of the cutting ring 40. Thus, the tissue clearing structure 48, shown as a tissue clearing ring 60, may be configured to rotate eccentrically about the spacer 46 and axle 38, with a point on the outer periphery of the tissue clearing structure 48 (e.g., the tissue clearing ring 60) moving outward of the outer circumference 54 of the cutting ring 40 and inward of the outer circumference 54 of the cutting ring 40 through a 360° revolution of the tissue clearing structure 48 (e.g., the tissue clearing ring 60) about the spacer 46 and axle 38.

The cutting rings 40 may be removably disposed on the axle 38 such that each of the cutting rings 40 may be replaceable independent of the remainder of the cutting rings 40. For example, any one of the first, second, third or fourth cutting rings 40a, 40b, 40c, 40d may be removed from the axle 38 without replacing the remainder of the cutting rings 40. For instance, a threaded nut 64, or other fastener (e.g., snap ring, pin, key, etc.) may be used to secure the cutting rings 40, spacers 46 and tissue clearing rings 60 on the axle 38. As shown in FIG. 3, the threaded nut 64 may threadably engage with a threaded portion 66 of the axle 38 and be tightened to fixedly secure the cutting rings 40 and spacers 46 on the axle 38 while the tissue clearing rings 60, positioned between adjacent cutting rings 40 remain free to move in a direction perpendicular to the central longitudinal axis X of the axle between adjacent cutting rings 40. The cutting rings 40, spacers 46 and/or tissue clearing rings 60 may be removed from the axle 38 by loosening the nut 64 and sliding the cutting rings 40, spacers 46, and/or tissue clearing rings 60 off the axle 38. Thus, one or more cutting rings 40, one or more spacers 46 and/or one or more tissue clearing rings 60 may be removed and/or replaced as desired. Accordingly, any of the cutting rings 40, spacers 46 and/or tissue clearing rings 60 may be replaceable independent of the remainder of the cutting rings 40, spacers 46 and/or tissue clearing rings 60. Furthermore, if a different spacing of cutting rings 40 is desired, the cutting rings 40, spacers 46, and tissue clearing rings 60 may be disassembled from the axle 38, and reassembled with different components (e.g., different cutting rings 40, spacers 46 and/or tissue clearing rings 60) to provide a different spacing of cutting rings 40 along the central longitudinal axis X of the axle 38.

Turning to FIG. 5, there is shown an exemplary way of creating perforations or cuts (e.g., slits) in a skin graft 70 using the cutting roller 20 and guide roller 22 of the skin graft mesher 10. The skin graft 70, which may be placed on a carrier 80, may be feed through the skin graft mesher 10 between the cutting roller 20 and the guide roller 22 to mesh the skin graft 70 (e.g., create a pattern of perforations or cuts in the skin graft 70).

The carrier 80 may be formed of any desired material. In some instances the carrier 80 may be a polymeric sheet (e.g., polypropylene or vinyl) configured to support the skin graft 70 as the skin graft 70 is advanced between the cutting roller 20 and the guide roller 22 of the skin graft mesher 10 while the cutting roller 20 and/or the guide roller 22 are being rotated.

For instance, the guide roller 22 may be rotated in a first direction (shown by the arrow A in FIG. 5), thus rotating the cutting roller 20 in a second, opposite direction (shown by the arrow B in FIG. 5) via the engagement of the drive mechanism (e.g. gears 34, 36) between the guide roller 22 and the cutting roller 20 while the carrier 80, with the skin graft 70 positioned thereon, is advanced between the cutting roller 20 and the guide roller 22 in a direction along arrow C of FIG. 5.

The guide roller 22 may be spaced apart from the cutting roller 20 a desired distance such that the cutting blades 50 of the cutting rings 40 of the cutting roller 20 penetrate into or through the skin graft 70 positioned on the carrier 80. For example, the distance between the cutting roller 20 and the guide roller 22 may be greater or smaller than the thickness of the skin graft 70, but less than the combined thickness of the skin graft 70 and the carrier 80 such that the cutting blades 50 penetrate entirely through the skin graft 70 and into the carrier 80, without penetrating entirely through the carrier 80, in some instances.

As the cutting roller 20 is rolled over skin graft 70 as the skin graft 70 is advanced between the cutting roller 20 and the guide roller 22, the cutting blades 50 of the plurality of cutting rings 40 penetrate into or through the skin graft 70 to form a pattern of perforations or cuts (e.g., slits) 72 in the skin graft 70 (only a portion of which are illustrated in FIG. 5). As the cutting blades 50 penetrate into or through the skin graft 70, portions of the skin graft 70 may be positioned between adjacent cutting rings 40.

Figure 6:
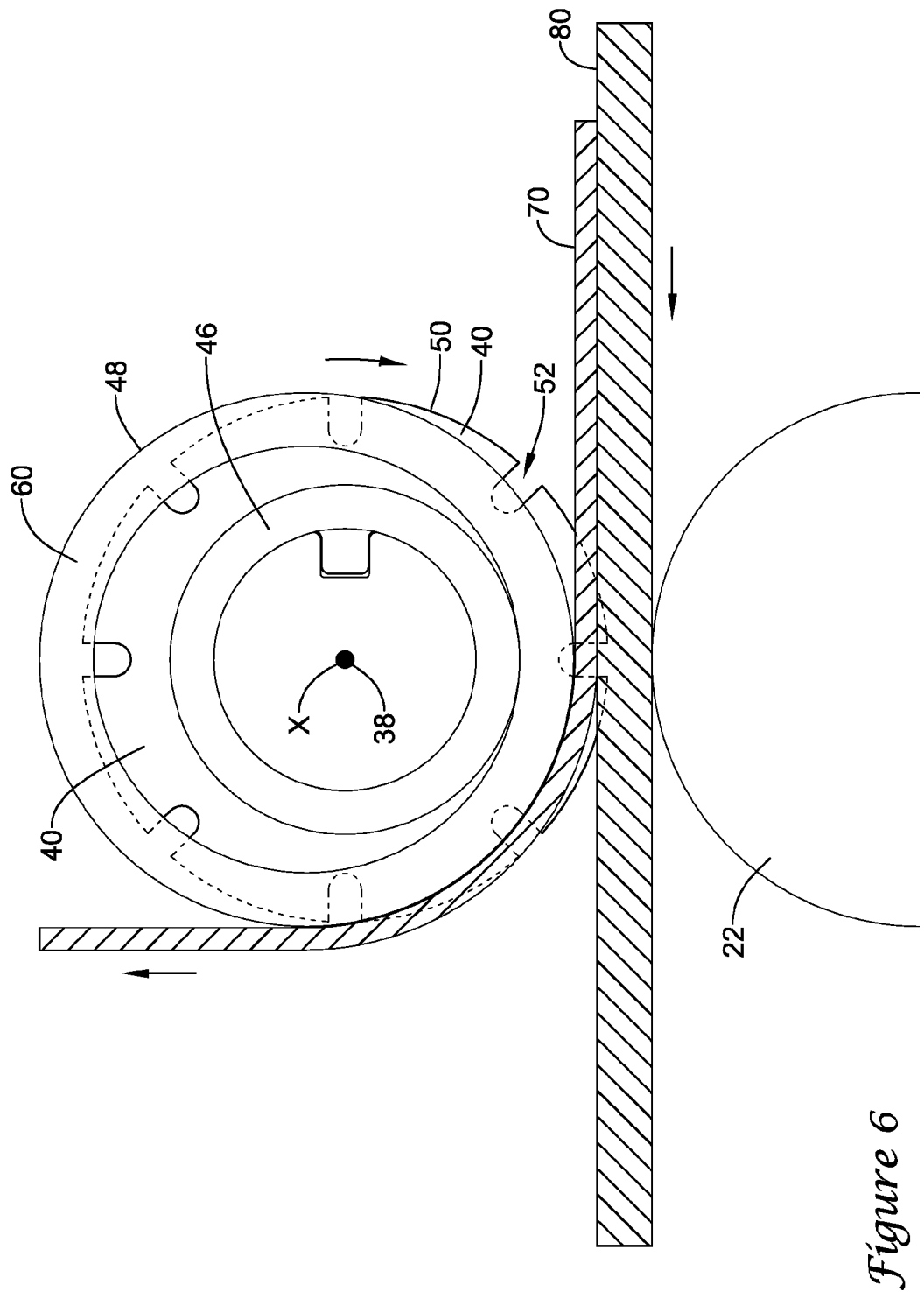
FIG. 6 is a cross-sectional view of the cutting roller while forming perforations or cuts in a skin graft.

FIG. 6 is a cross-sectional view illustrating an exemplary interaction of the components of the cutting roller 20 with the skin graft 70. For example, FIG. 6 illustrates cutting blades 50 of a cutting ring 40 penetrating through the skin graft 70 and into the carrier 80 underlying the skin graft 70, causing portions of the skin graft 70 to be positioned in the space between adjacent cutting rings 40 (e.g., located radially inward of the outer circumference of the cutting ring 40).

As the skin graft 70 moves past the cutting roller 20, portions of tissue of the skin graft 70 may have a tendency to stick or cling to the cutting rings 40 between adjacent cutting rings 40. Accordingly, the tissue clearing structures 48, positioned between adjacent cutting rings 40, may disengage portions of tissue of the skin graft from between adjacent cutting rings 40 by pushing the tissue radially outward beyond the outer diameter of the cutting rings 40 of the cutting roller 20 subsequent to forming perforations or cuts (e.g., slits) 72 in the skin graft 70. Thus, the cutting rings 40 may remain substantially clear of tissue during each subsequent revolution of the cutting roller 20.

An exemplary tissue clearing structure 48, arranged on the cutting roller 20 between adjacent cutting rings 40 with the axle 38 rotatably positioned through an opening of the tissue clearing structure 48, configured to push tissue radially outward is shown in FIG. 6. As shown in FIG. 6, the tissue clearing structure 48, shown as a tissue clearing ring 60, may be eccentrically positioned on the axle 38 around the spacer 46 between adjacent cutting rings 40 and rotatable relative to the spacer 46. The tissue clearing ring 60 may be freely rotatable relative to the cutting rings 40 and axle 38 of the cutting roller 20 about an axis offset from the central longitudinal axis X of the axle 38 and/or the tissue clearing ring 60 may be freely movable in a perpendicular direction to the central longitudinal axis X of the axle 38. In some instances, the spacer 46 may be eccentrically positioned in the opening of the tissue clearing ring 60 and rotatable relative thereto, while the spacer 46 may be coaxially positioned around and may or may not be rotatable relative to the axle 38. In other embodiments, the tissue clearing ring 60 may include an eccentrically positioned opening extending through the tissue clearing ring 60 through which the axle 38 may be rotatably positioned, with or without the inclusion of a spacer 46.

As the skin graft 70 is passed between the cutting roller 20 and the guide roller 22, the portion of the skin graft 70 located between the cutting roller 20 and the guide roller 22 may push the tissue clearing ring 60 away from the guide roller 22 in a direction generally perpendicular to the central longitudinal axis X and along a plane passing through the central longitudinal axis X of the cutting roller 20 and the central longitudinal axis of the guide roller 22 (upward in FIG. 6), permitting the cutting blades 50 of the cutting rings 40 to extend radially outward of the tissue clearing ring 60 (e.g., extend radially outward beyond the outer perimeter or circumference of the tissue clearing ring 60) and penetrate into or through the skin graft 70. While a first portion of the cutting rings 40 are exposed and extend radially outward beyond the outer perimeter or circumference of the tissue clearing ring 60, a second portion of the cutting rings 40 (e.g. located opposite the first portion) are covered by the tissue clearing ring 60 and do not extend radially outward beyond the outer perimeter or circumference of the tissue clearing ring 60. Thus, the tissue clearing ring 60 may extend radially outward beyond the outer diameter of the cutting ring 40 around less than the entire outer circumference of the cutting ring 40. In other words, a first point on an outer periphery of the tissue clearing ring 60 may extend radially outward from the longitudinal axis X of the axle 38 to or beyond the outer circumference of the cutting rings 40 while a second point on the outer periphery of the tissue clearing ring 60 does not extend radially outward from the longitudinal axis X of the axle 38 to the outer circumference of the cutting rings 40. In some instances, the tissue clearing ring 60 may be dimensioned such that while one point on the perimeter of the opening of the tissue clearing ring 60 contacts the spacer 46, another point on the outer perimeter or circumference of the tissue clearing ring 60 extends beyond the outer circumference of the cutting rings 40 (e.g., radially outward from the longitudinal axis X of the axle 38 to or beyond the outer circumference of the cutting rings 40).

After the skin graft 70 passes between the cutting roller 20 and the guide roller 22, the portion of the tissue clearing ring 60 extending radially outward to or beyond the outer circumference of the cutting rings 40 may push or urge the tissue of the skin graft 70 outward from between the adjacent cutting rings 40, clearing the space between the adjacent cutting rings 40 from tissue of the skin graft 70. Thus, the tissue clearing rings 60 may separate the skin graft 70 from the cutting rings 40 of the cutting roller 20 after forming perforations or cuts 72 in the skin graft 70.

Figure 7:
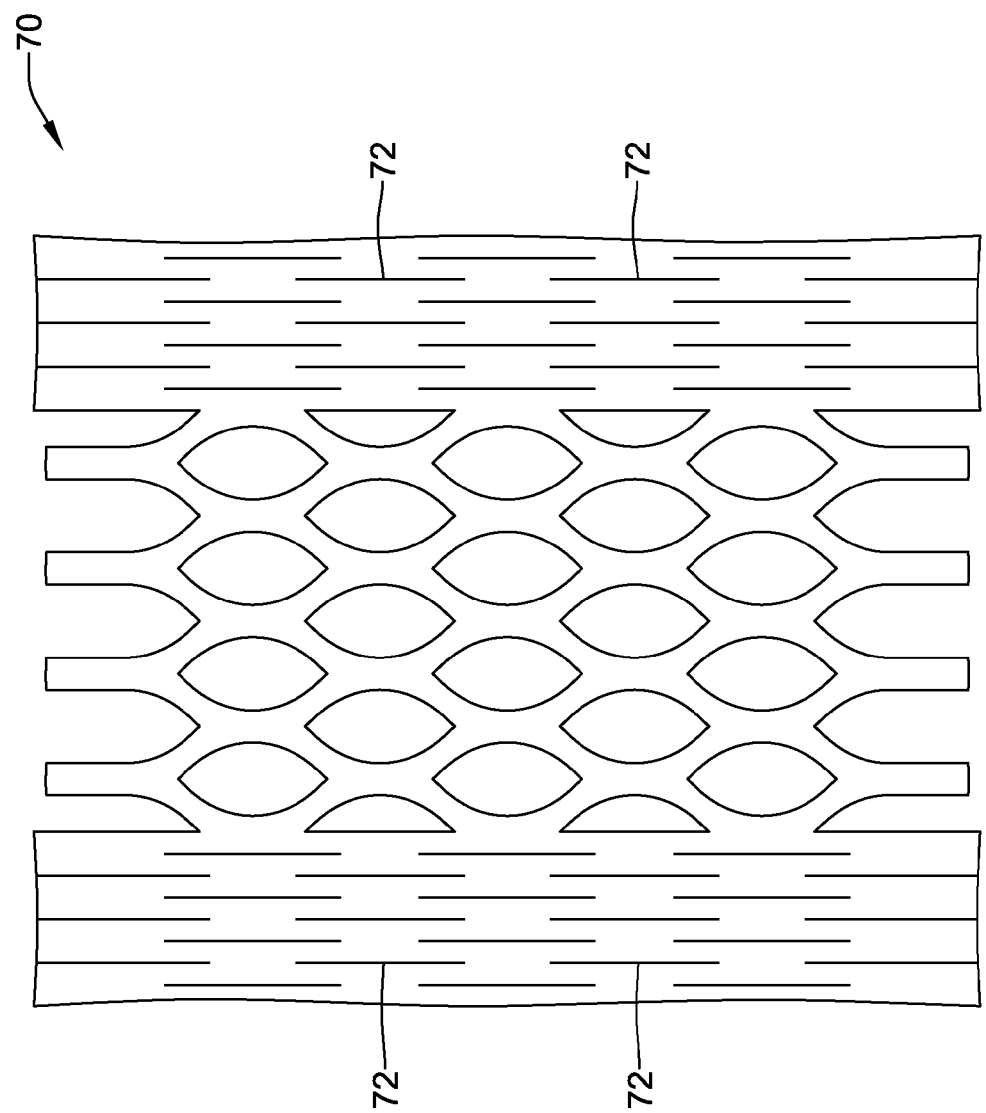
FIG. 7 is a plan view of a skin graft having perforations or cuts formed therein.

An exemplary skin graft 70 which has been passed through the skin graft mesher 10 is illustrated in FIG. 7. The processed skin graft 70 may include a pattern of perforations or cuts 72 formed therein. It is noted that the relative dimensions of the length of the perforations or cuts 72, the length of remaining tissue between adjacent perforations or cuts 72 along the same longitudinal line, and/or the width of tissue between adjacent rows of perforations or cuts 72 are for illustrative purposes only, and actual dimensions may vary as dictated by the configuration and/or spacing of cutting rings 40 used. The pattern of perforations or cuts 72 may be dictated by the configuration and arrangement of cutting rings 40 mounted on the cutting roller 20. For example, the processed skin graft 70 may include a plurality of parallel rows of discontinuous perforations or cuts 72. Each row of discontinuous perforations or cuts 72 may include perforated or cut portions alternating with uncut portions of the skin graft 70. In the illustrated embodiment, perforations or cuts 72 along one row may be oriented beside uncut portions of adjacent rows. In other words, to each side of a cut portion of a row, an uncut portion of an adjacent row may be provided and, conversely, to each side of an uncut portion of a row, a cut portion of an adjacent row may be provided.

The formation of the pattern or perforations or cuts 72 on the skin graft 70 (e.g., meshing) may permit the skin graft 70 to be stretched to a desired ratio of expansion, such as a 1.5:1, 3:1, 6:1, 9:1, 12:1 or 15:1 ratio of expansion for use in a skin grafting procedure. The distance between adjacent rows of discontinuous perforations or cuts 72 and/or the length of perforations or cuts 72 may dictate, at least in part, the amount of expansion permitted. Thus, unlike prior art meshers in which the minimum distance between adjacent rows of cuts is about 1.2 millimeters, at least some embodiments of the cutting roller 20 described herein, can form adjacent rows of cuts 72 at a distance of 0.8 millimeters or less, 0.6 millimeters or less, 0.4 millimeters or less, or less than 0.8 millimeters, 0.6 millimeters, or 0.4 millimeters in some instances. The reduced distance between adjacent rows may permit a greater ratio of expansion of the skin graft 70 over known prior art skin graft meshers, while providing a similar medical efficiency ("take") of the skin graft 70.

Figure 8:
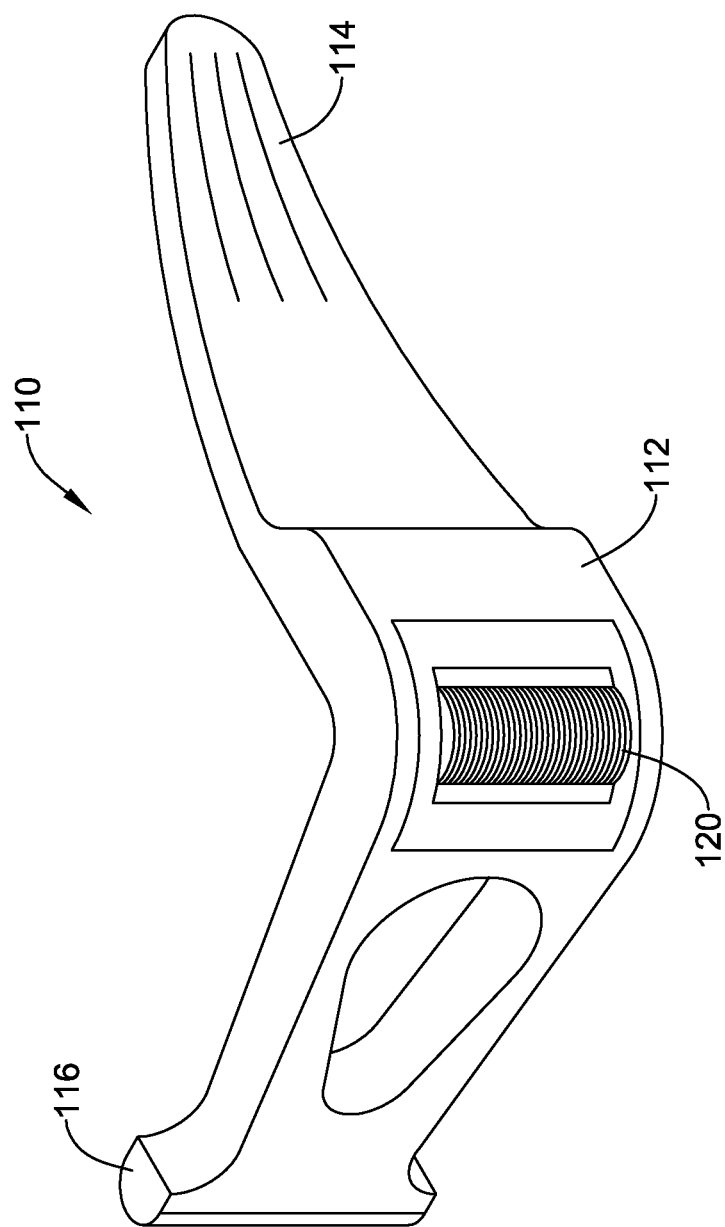
FIG. 8 is a perspective view of an exemplary handheld skin graft preparation device.

A handheld skin graft preparation device 110 is shown in FIG. 8. In some instances, the handheld skin graft preparation device 110 may be a skin graft mesher configured to mesh a skin graft, or the handheld skin graft preparation device 110 may be a skin graft mincer configured mince a skin graft for use during a medical procedure.

The handheld device 110 may include a body 112 having a first handle portion 114 and a second handle portion 116 to be grasped by medical personnel to manipulate the device 110 when preparing a skin graft. The body 112 may be formed of any desired material, such as a metallic material (e.g., stainless steel) or a polymeric material (e.g., PEEK).

Figure 9:
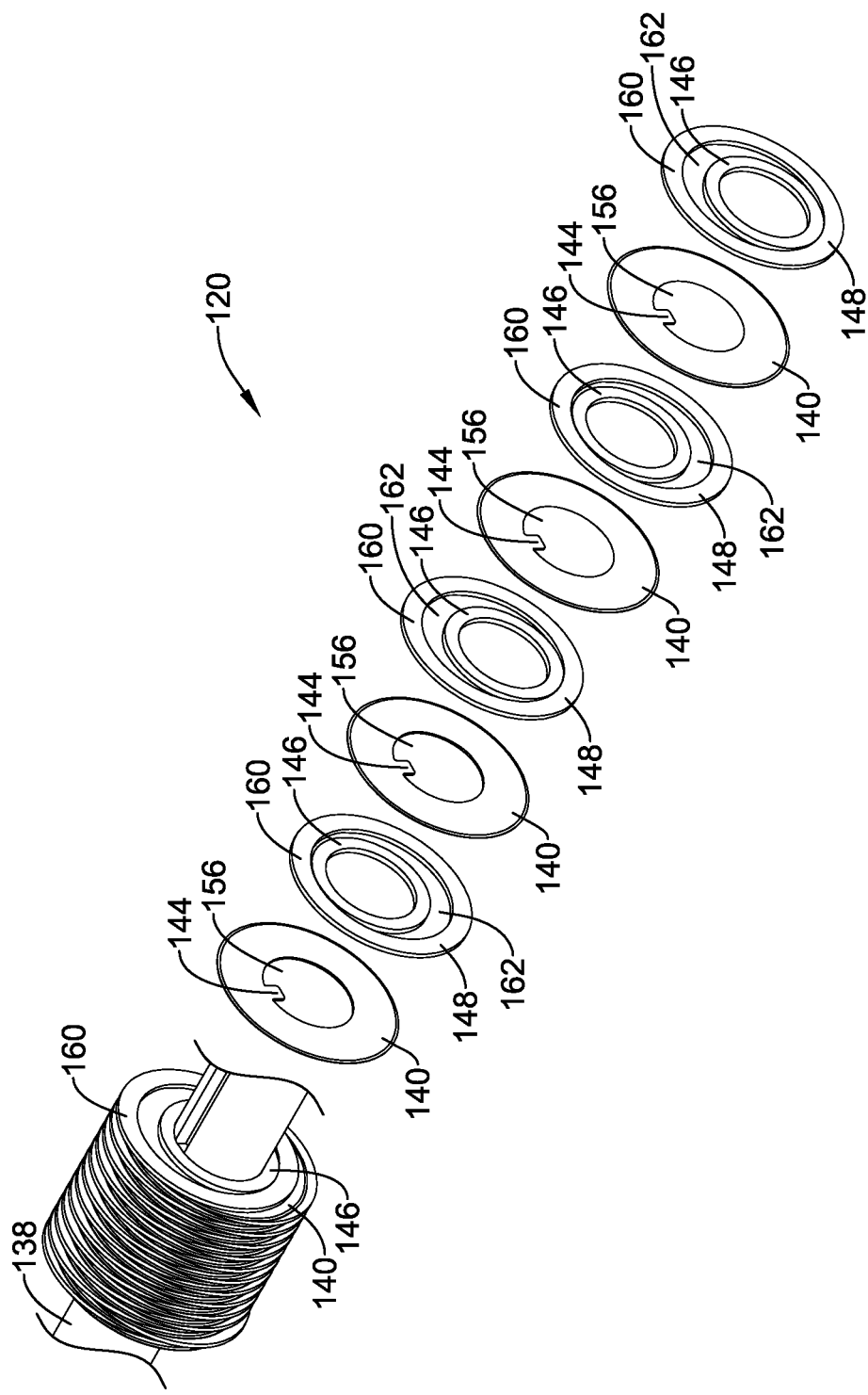
FIG. 9 is an exploded view of an exemplary cutting roller of the handheld skin graft preparation device of FIG. 8.

The handheld device 110 may include a cutting member, shown as a cutting roller 120, rotatably mounted to the body 112. Although dimensions may be different, the cutting roller 120 may be similar to the cutting roller 20 described above in many aspects. For example, turning to FIG. 9, the cutting roller 120 may include an axle 138 rotatable with respect to the body 112, similar to the axle 38, with a plurality of cutting segments, shown as cutting rings 140, mounted thereon and rotatable with the axle 138, similar to the cutting rings 40. The cutting rings 140 may include an opening 156 through which the axle 138 may extend and a keying interface, such as the key 144 configured to interface with the longitudinal slot of the axle 138 such that the cutting rings 140 are rotatable with the axle 138. The cutting roller 120 may also include spacers 146 positioned between adjacent cutting rings 140 configured to space adjacent cutting rings 140 a desired distance apart.

Similar to the cutting roller 20, the cutting roller 120 may also include a tissue clearing structure 148 (e.g. tissue clearing ring 160) positioned between adjacent cutting rings 140, surrounding and freely rotatable about the axle 138 and spacer 146. The tissue clearing structure 148 may be configured to clear tissue from between adjacent cutting rings 140 during operation of the handheld device 110, as described above. The tissue clearing structure 148 (e.g., tissue clearing ring 160) may include an opening 162 through which the axle 138 extends and within which the spacer 146 is positioned. Similar to the tissue clearing structure 48 described above, the tissue clearing structure 148, shown as a tissue clearing ring 160, may be configured to rotate eccentrically about the spacer 146 and axle 138, such that a point on the outer periphery of the tissue clearing structure 148 (e.g., the tissue clearing ring 160) may move outward of the outer circumference 154 of the cutting ring 140 and inward of the outer circumference 154 of the cutting ring 140 through a 360° revolution of the tissue clearing structure 148 (e.g., the tissue clearing ring 160) about the spacer 146 and axle 138.

Figure 10:
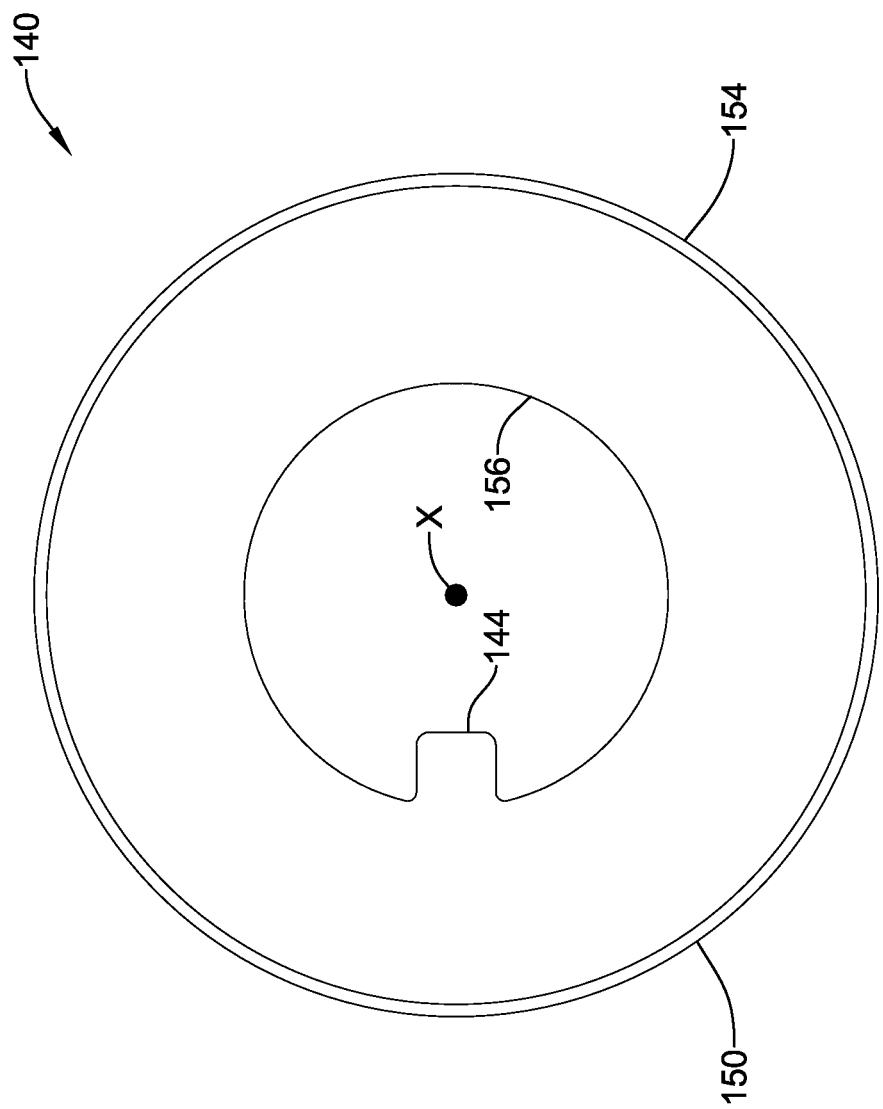
FIG. 10 is a plan view of an exemplary cutting ring for use in a skin graft preparation device for mincing a skin graft.

If used in a meshing application, the cutting rings 140 may be serrated or include notches, similar to the cutting rings 40, defining discrete, spaced apart cutting blades around the circumference of the cutting rings 140. However, if used in a mincing application (e.g., an application in which the cutting roller 120 is rolled over the skin graft in a first direction and then rolled over the skin graft in a second direction transverse to the first direction to mince the skin graft into small pieces), the cutting rings 140 may include a continuous cutting blade 150 extending around the entire circumference 154 of the cutting ring 140, as shown in FIG. 10.

In use, the handheld device 110 may be positioned on the skin graft and the cutting roller 120 rolled over the skin graft to create cuts in the skin graft. If serrated cutting rings 40 having discontinuous cutting blades are utilized, the cuts may be discontinuous staggered cuts, permitting the skin graft to be expanded as shown in FIG. 7 for use in a skin grafting procedure. If the cutting rings 140 having continuous cutting blades are utilized, the skin graft may be cut into strips of tissue. Subsequent cutting of the strips in a transverse direction may mince the skin graft into small pieces to be used in a grafting procedure.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:
1. A skin graft preparation device, comprising:
a housing; and
a cutting member rotatably mounted to the housing, the cutting member including:
an axle having a longitudinal axis;
a plurality of cutting segments disposed on the axle and rotatable with the axle through rotation of the axle about the longitudinal axis;
a tissue clearing structure of a plurality of tissue clearing structures,
wherein the tissue cutting structures are individually positioned between adjacent cutting segments with the axle extending through the tissue clearing structure and rotatable independently of the tissue clearing structure;
the tissue clearing structure configured to clear tissue from between adjacent cutting segments during operation of the skin graft preparation device.

2. The skin graft preparation device of claim 1, wherein the tissue clearing structure extends radially outward beyond an outer diameter of the plurality of cutting segments around less than an entire outer circumference of the plurality of cutting segments.

3. The skin graft preparation device of claim 1, wherein the tissue clearing structure is a tissue clearing ring disposed circumferentially around the axle.

4. The skin graft preparation device of claim 3, wherein the tissue clearing ring is moveable in a direction perpendicular to the longitudinal axis of the axle.

5. The skin graft preparation device of claim 3, wherein the tissue clearing ring is eccentrically positioned relative to the longitudinal axis of the axle.

6. The skin graft preparation device of claim 1, wherein the plurality of cutting segments are a plurality of cutting rings.

7. The skin graft preparation device of claim 6, wherein each of the cutting rings is spaced away from an adjacent cutting ring along the longitudinal axis.

8. A skin graft preparation device, comprising:
a housing;
an axle having a longitudinal axis, the axle rotationally mounted to the housing;
a plurality of cutting segments disposed on the axle and rotatable with the axle through rotation of the axle, each cutting segment having an outer circumference and an outer diameter; and
a tissue clearing structure of a plurality of tissue clearing structures positioned on and rotatable about the axle between adjacent cutting segments, the tissue clearing structure extending radially outward beyond the outer diameter of the cutting segments around less than the entire outer circumference of the cutting segments.

9. The skin graft preparation device of claim 8, wherein the tissue clearing structure is eccentrically rotatable about the axle.

10. The skin graft preparation device of claim 9, wherein the tissue clearing structure is moveable in a direction perpendicular to the longitudinal axis of the axle.

11. The skin graft preparation device of claim 8, wherein each of the plurality of cutting segments is a cutting ring spaced away from adjacent cutting rings by a distance of 0.8 millimeters or less.

12. The skin graft preparation device of claim 8, wherein the plurality of cutting segments are a plurality of cutting rings arranged along the longitudinal axis of the axle.

13. A skin graft preparation device, comprising:
a housing;
an axle having a longitudinal axis, the axle rotatably mounted to the housing;
a first cutting segment disposed on the axle and rotatable with the axle through rotation of the axle, the first cutting segment including one or more cutting blades circumferentially arranged around an outer perimeter of the first cutting segment;
a second cutting segment disposed on the axle and rotatable with the axle through rotation of the axle, the second cutting segment including one or more cutting blades circumferentially arranged around an outer perimeter of the second cutting segment;
a third cutting segment disposed on the axle and rotatable with the axle through rotation of the axle, the third cutting segment including one or more cutting blades circumferentially arranged around an outer perimeter of the third cutting segment;
a fourth cutting segment disposed on the axle and rotatable with the axle through rotation of the axle, the fourth cutting segment including one or more cutting blades circumferentially arranged around an outer perimeter of the fourth cutting segment;
a first tissue clearing structure positioned on the axle between the first and second cutting segments, wherein a first point on an outer periphery of the first tissue clearing structure extends radially outward from the longitudinal axis of the axle to or beyond the outer perimeters of the first and second cutting segments while a second point on the outer periphery of the first tissue clearing structure does not extend radially outward from the longitudinal axis of the axle to the outer perimeters of the first and second cutting segments;
a second tissue clearing structure positioned on the axle between the second and third cutting segments, wherein a first point on an outer periphery of the second tissue clearing structure extends radially outward from the longitudinal axis of the axle to or beyond the outer perimeters of the second and third cutting segments while a second point on the outer periphery of the second tissue clearing structure does not extend radially outward from the longitudinal axis of the axle to the outer perimeters of the second and third cutting segments;
a third tissue clearing structure positioned on the axle between the third and fourth cutting segments, wherein a first point on an outer periphery of the third tissue clearing structure extends radially outward from the longitudinal axis of the axle to or beyond the outer perimeters of the third and fourth cutting segments while a second point on the outer periphery of the third tissue clearing structure does not extend radially outward from the longitudinal axis of the axle to the outer perimeters of the third and fourth cutting segments.

14. The skin graft preparation device of claim 13, wherein the first, second, and third tissue clearing structures are first, second and third tissue clearing rings, respectively.

15. The skin graft preparation device of claim 14, wherein each of the first, second and third tissue clearing rings is positioned on the axle and moveable in a direction perpendicular to the longitudinal axis of the axle.

16. The skin graft preparation device of claim 13, further comprising:
a first spacer positioned on the axle between the first and second cutting segments configured to space the first cutting segment away from the second cutting segment a predetermined distance;
a second spacer positioned on the axle between the second and third cutting segments configured to space the second cutting segment away from the third cutting segment a predetermined distance; and
a third spacer positioned on the axle between the third and fourth cutting segments configured to space the third cutting segment away from the fourth cutting segment a predetermined distance.

17. The skin graft preparation device of claim 16, wherein:
the first tissue clearing structure is a first tissue clearing ring disposed circumferentially around the first spacer;
the second tissue clearing structure is a second tissue clearing ring disposed circumferentially around the second spacer; and
the third tissue clearing structure is a third tissue clearing ring disposed circumferentially around the third spacer.

18. The skin graft preparation device of claim 13, wherein:
the first cutting segment is spaced away from the second cutting segment by a distance of 0.8 millimeters or less;
the second cutting segment is spaced away from the third cutting segment by a distance of 0.8 millimeters or less; and
the third cutting segment is spaced away from the fourth cutting segment by a distance of 0.8 millimeters or less.

19. The skin graft preparation device of claim 13, wherein each of the first, second, third and fourth cutting segments is removably disposed on the axle such that each of the first, second, third and fourth cutting segments is replaceable independent of the remainder of the cutting segments.

20. The skin graft preparation device of claim 13, wherein each of the first, second, third and fourth cutting segments includes a plurality of circumferentially arranged cutting blades, and wherein the second cutting segment is disposed on the axle such that the cutting blades of the second cutting segment are not axially aligned with the cutting blades of the first cutting segment.

21. The skin graft preparation device of claim 20, wherein the third cutting segment is disposed on the axle such that the cutting blades of the third cutting segment are not axially aligned with the cutting blades of the second cutting segment.

22. The skin graft preparation device of claim 21, wherein the cutting blades of the third cutting segment are axially aligned with the cutting blades of the first cutting segment.

23. The skin graft preparation device of claim 22, wherein the fourth cutting segment is disposed on the axle such that the cutting blades of the fourth cutting segment are not axially aligned with the cutting blades of the third cutting segment and the cutting blades of the fourth cutting segment are axially aligned with the cutting blades of the second cutting segment.

24. The skin graft preparation device of claim 13, wherein each of the first, second, third and fourth cutting segments includes a keying interface mating with a keying interface of the axle.

\* \* \* \* \*

UNITED STATES PATENT AND TRADEMARK OFFICE
CERTIFICATE OF CORRECTION

| | | |
|---|---|---|
| PATENT NO. | : 9,055,970 B2 | Page 1 of 1 |
| APPLICATION NO. | : 13/650271 | |
| DATED | : June 16, 2015 | |
| INVENTOR(S) | : Aleksandr Zolotov | |

It is certified that error appears in the above-identified patent and that said Letters Patent is hereby corrected as shown below:

IN THE CLAIMS

In column 12, line 60, in Claim 2, after "claim 1,", delete "¶", therefor

Signed and Sealed this
Fifteenth Day of March, 2016

Michelle K. Lee
*Director of the United States Patent and Trademark Office*